United States Patent
Morgan et al.

(10) Patent No.: US 6,241,751 B1
(45) Date of Patent: Jun. 5, 2001

(54) DEFIBRILLATOR WITH IMPEDANCE-COMPENSATED ENERGY DELIVERY

(75) Inventors: Carlton B. Morgan, Bainbridge Island; Bradford E. Gliner, Issaquah; Kent W. Leyde, Redmond; Thomas D. Lyster, Bothell, all of WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/299,455

(22) Filed: Apr. 22, 1999

(51) Int. Cl.[7] .................................................. A61N 1/39
(52) U.S. Cl. ................................................................ 607/8
(58) Field of Search ........................ 607/4, 5, 8; 600/547

(56) References Cited

U.S. PATENT DOCUMENTS

| | | |
|---|---|---|
| 4,328,808 | 5/1982 | Charbonnier et al. . |
| 4,785,812 | 11/1988 | Pihl et al. . |
| 4,850,356 * | 7/1989 | Heath ........................................ 607/5 |
| 5,111,813 * | 5/1992 | Charbonnier et al. ................... 607/5 |
| 5,199,429 | 4/1993 | Kroll et al. ........................... 128/419 |
| 5,385,575 | 1/1995 | Adams .................................... 607/5 |
| 5,514,160 | 5/1996 | Kroll et al. .............................. 607/5 |
| 5,591,211 | 1/1997 | Meltzer .................................... 607/5 |
| 5,634,938 | 6/1997 | Swanson et al. ........................ 607/5 |
| 5,733,309 | 3/1998 | Kroll et al. .............................. 607/5 |
| 5,733,310 | 3/1998 | Lopin et al. .............................. 607/7 |
| 5,749,904 | 5/1998 | Gliner et al. ............................. 607/7 |
| 5,836,972 | 11/1998 | Stendahl et al. ......................... 607/5 |
| 6,047,212 * | 4/2000 | Gliner et al. ............................. 607/7 |

FOREIGN PATENT DOCUMENTS

| | | |
|---|---|---|
| 0590318A1 | 8/1993 | (EP) . |
| WO94/21327 | 3/1993 | (WO) . |

\* cited by examiner

*Primary Examiner*—Jeffrey R. Jastrzab

(57) ABSTRACT

A defibrillator having an energy storage capacitor network with multiple configurations selected according to patient impedance and desired energy level for delivery of an impedance-compensated defibrillation pulse is provided. The set of configurations may include series, parallel, and series/parallel combinations of energy storage capacitors within the energy storage capacitor network. The impedance-compensated defibrillation pulse may be delivered over an expanded range of energy levels while limiting the peak current to levels that are safe for the patient using configurations tailored for lower impedance patients and limiting the range of defibrillation pulse durations and providing adequate current levels for higher impedance patients. Configurations of the energy storage capacitor network may be readily added to extend the range of energy levels well above 200 joules.

38 Claims, 10 Drawing Sheets

DEFIBRILLATOR WITH IMPEDANCE-COMPENSATED ENERGY DELIVERY

BACKGROUND OF THE INVENTION

This invention relates to electrotherapy circuits and in particular to a defibrillator using multiple capacitors to provide for an impedance-compensated delivery of defibrillation pulses to the patient.

Electro-chemical activity within a human heart normally causes the heart muscle fibers to contract and relax in a synchronized manner that results in the effective pumping of blood from the ventricles to the body's vital organs. Sudden cardiac death is often caused by ventricular fibrillation (VF) in which abnormal electrical activity within the heart causes the individual muscle fibers to contract in an unsynchronized and chaotic way. The only effective treatment for VF is electrical defibrillation in which an electrical shock is applied to the heart to allow the heart's electro-chemical system to re-synchronize itself. Once organized electrical activity is restored, synchronized muscle contractions usually follow, leading to the restoration of cardiac rhythm.

The minimum amount of patient current and energy delivered that is required for effective defibrillation depends upon the particular shape of the defibrillation waveform, including its amplitude, duration, shape (such as sine, damped sine, square, exponential decay), and whether the current waveform has a single polarity (monophasic), both negative and positive polarities (biphasic) or multiple negative and positive polarities (multiphasic). At the same time, there exists a maximum value of current in the defibrillation pulse delivered to the patient above which will result in damage to tissue and decreased efficacy of the defibrillation pulse.

Peak current is the highest level of current that occurs during delivery of the defibrillation pulse. Limiting peak currents to less than the maximum value in the defibrillation pulse is desirable for both efficacy and patient safety. Because the transthoracic impedance ("patient impedance") of the human population may vary across a range spanning 20 to 200 ohms, it is desirable that an external defibrillator provide an impedance-compensated defibrillation pulse that delivers a desired amount of energy to any patient with the range of patient impedances and with peak currents limited to safe levels substantially less than the maximum value.

Most external defibrillators employ a single energy storage capacitor or a fixed bank of energy storage capacitors charged to a single voltage level. Controlling the amount of energy delivered to any given patient across the range of patient impedances is a problem commonly solved by controlling the "tilt" or difference between initial and final voltages of the energy storage capacitor as well as the discharge time of the defibrillation pulse. Most external defibrillators use a single energy storage capacitor charged to a fixed voltage level resulting in a broad range of possible discharge times and tilt values across the range of patient impedances. A method of shaping the waveform of the defibrillation pulse in terms of duration and tilt is discussed in U.S. Pat. No. 5,607,454, "Electrotherapy Method and Apparatus", issued Mar. 4, 1997 to Gliner et al. Using a single capacitor to provide the defibrillation pulse at adequate energy levels across the entire range of patient impedances can result in high peak currents being delivered to patients with relatively low impedances. At the same time, the charge voltage of the energy storage capacitor must be adequate to deliver a defibrillation pulse with the desired amount of energy to patients with high impedances.

Various prior art solutions to the problem of high peak currents exist. One method involves placing resistors in series with the energy storage capacitor to prevent excessive peak currents to low impedance patients. In U.S. Pat. No. 5,514,160, "Implantable Defibrillator For Producing A Rectangular-Shaped Defibrillation Waveform", issued May 7, 1996, to Kroll et al., an implantable defibrillator have a rectilinear-shaped first phase uses a MOSFET operating as a variable resistor in series with the energy storage capacitor to limit the peak current. In U.S. Pat. No. 5,733,310, "Electrotherapy Circuit and Method For Producing Therapeutic Discharge Waveform Immediately Following Sensing Pulse", issued Mar. 31, 1998, to Lopin et al., an electrotherapy circuit senses patient impedance and selects among a set of series resistors in series with the energy storage capacitor to create a sawtooth approximation to a rectilinear shape in the defibrillation pulse. Using current limiting resistors as taught by the prior art results in substantial amounts of power being dissipated in the resistors, which increases the energy requirements on the defibrillator battery.

Another approach to limiting peak currents involves using multiple truncated decaying exponential waveforms from multiple capacitors to form a sawtooth approximation of a rectilinear shape of the discharge waveform in an implantable defibrillator. In U.S. Pat. No. 5,199,429, "Implantable Defibrillation System Employing Capacitor Switching Networks", issued Apr. 6, 1993, to Kroll et al., a set of energy storage capacitors are charged and then successively discharged during the first phase to create the sawtooth pattern. Kroll et al. teach that multiple capacitors may be arbitrarily arranged in series, parallel, or series-parallel arrangements during the delivery of the defibrillation pulse in order to tailor the shape of the defibrillation waveform with a high degree of flexibility.

In U.S. Pat. No. 5,836,972, "Parallel Charging of Mixed Capacitors", issued Nov. 17, 1998, to Stendahl et al., a method for charging banks of energy storage capacitors in parallel is taught. The banks of energy storage capacitors may then be coupled in series in order to deliver a defibrillation pulse.

However, neither Kroll et al. nor Stendahl et al. address the issue of obtaining impedance-compensated defibrillation pulses which have peak currents less than the maximum value and with less variation of discharge times across the range of patient impedances. It would therefore be desirable to provide a defibrillator that selects among configurations of energy storage capacitors to deliver an impedance-compensated defibrillation pulse to the patient.

SUMMARY OF THE INVENTION

A defibrillator having an energy storage capacitor network with a set of configurations selected according to patient impedance and desired energy level for delivery of an impedance-compensated defibrillation pulse is provided. Impedance-compensation according to the present invention means providing an energy storage capacitor network with an overall capacitance and charge voltage that are tailored to the patient impedance and the desired energy level. The peak current is limited to values less than the maximum value for low patient impedances while the variation of discharge times of the defibrillation pulse is reduced for high impedance patients.

The set of configurations of the energy storage capacitor network may include various series, parallel, and series/parallel combinations of energy storage capacitors within the energy storage capacitor network that are selected as a function of patient impedance to provide a variety of overall capacitances and charge voltages. The impedance-compensated defibrillation pulse may be delivered over an expanded range of energy levels while limiting the peak current to levels that are safe for the patient using configurations tailored for lower impedance patients. At the same time, adequate current levels are delivered using selected configurations tailored for high impedance patients. Other configurations may be readily added to the energy storage capacitor network to extend the range of available energy levels well above 200 joules.

The defibrillator according to the present invention is constructed using an energy storage capacitor network using at least two capacitors that store energy for delivery of the defibrillation pulse to the patient. The defibrillator is typically portable and operates using a conventional battery as an energy source. A high voltage charger operates to charge the capacitors in the energy storage capacitor network to desired voltage levels. An HV switch couples the capacitors across the patient according to a desired pulse duration and polarity. In the preferred embodiment, the HV switch comprises an "H bridge" consisting of four commutating switches for applying a biphasic defibrillation pulse to the patient through a pair of electrodes.

A controller controls the process of charging the energy storage capacitor network. Responsive to a press of a shock button, the controller delivers the impedance-controlled defibrillation pulse to the patient by selecting the configuration of the energy storage capacitor network and controlling the HV switch to obtain the desired duration and polarity of the impedance-compensated defibrillation pulse.

Measuring the patient impedance may be done immediately before delivery of the defibrillation pulse. Based on the patient impedance, an appropriate configuration of capacitors may be selected to deliver the impedance-compensated defibrillation pulse at the desired energy level while limiting the peak current to levels that are safe for the patient.

The energy level of the impedance-compensated defibrillation pulse may be readily selected according to the present invention. The energy storage capacitor network has a set of configurations tailored to the patient impedance and the desired energy level. The controller selects the appropriate configuration after determining the patient impedance and the desired energy level. Defibrillator applications involving selectable energy levels in excess of 200 joules (j) can benefit from using impedance-compensated defibrillation pulses because the peak currents can be limited to less than the maximum value across a wider range of patient impedances and energy levels.

An alternative embodiment of the present invention provides for the energy storage capacitor network that employs parallel combinations of capacitors and resistors that deliver energy for the defibrillation pulse using blocking diodes in place of switches. In this way, an impedance-matched defibrillation pulse may be delivered without the active intervention of the controller to measure the patient impedance and select the various configurations of capacitors. Component count would be substantially reduced over that of the first embodiment but at the expense of flexibility and the ability to select energy levels.

One feature of the present invention is to provide a defibrillator that delivers impedance-compensated defibrillation pulses with a selected amount of energy.

A further feature of the present invention is to provide a defibrillator that delivers impedance-compensated defibrillation pulses using multiple capacitors.

Another feature of the present invention is to provide a method of delivering impedance-compensated defibrillation pulses by selecting among a set of configurations of the energy storage capacitor network.

A further feature of the present invention is to provide an energy storage capacitor network for a defibrillator that is capable of delivering impedance-compensated defibrillation pulses with energy levels above 200 joules.

Another feature of the present invention is to provide an energy storage capacitor network using diode switching to deliver impedance-compensated defibrillation pulses.

Other features, attainments, and advantages will become apparent to those skilled in the art upon a reading of the following description when taken in conjunction with the accompanying drawings.

DETAILED DESCRIPTION OF THE INVENTION

Figure 1:
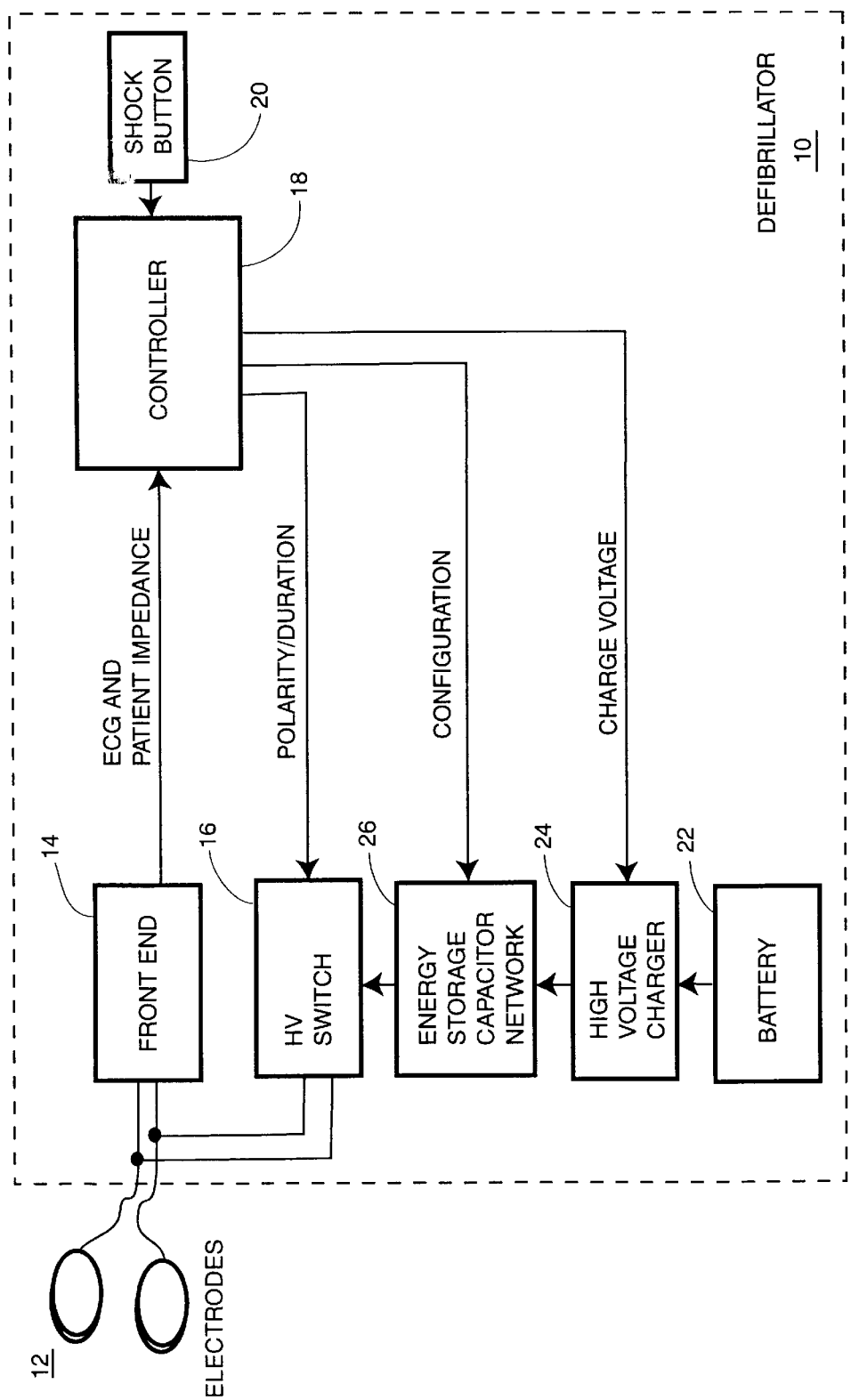
FIG. 1 is a simplified block diagram of a defibrillator with an energy storage capacitor network according to the present invention.

FIG. 1 is a simplified block diagram of a defibrillator 10 according to the present invention. A pair of electrodes 12 for coupling to a patient (not shown) are connected to a front end 14 and further connected to an HV switch 16. The front end 14 provides for detection, filtering, and digitizing of the ECG signal from the patient. The ECG signal is in turn provided to a controller 18 which runs a shock advisory algorithm that is capable of detecting ventricular fibrillation (VF) or other shockable rhythm that is susceptible to treatment by electrotherapy.

The front end 14 is preferably capable of measuring the patient impedance across the electrodes 12 using a low level test signal. The patient impedance may be measured and digitized in the front end 14 using an analog to digital converter (not shown) in order to provide the patient impedance data to the controller 18. The patient impedance may also be measured using a variety of other methods such as by delivering a low-level non-therapeutic pulse to the patient prior to delivery of the defibrillation pulse and measuring the voltage drop across the electrodes 12.

A shock button 20, typically part of a user interface of the defibrillator 10 allows the user to initiate the delivery of a defibrillation pulse through the electrodes 12 after the controller 18 has detected VF or other shockable rhythm. A battery 22 provides power for the defibrillator 10 in general and in particular for a high voltage charger 24 which charges the capacitors in an energy storage capacitor network 26. Typical battery voltages are 12 volts or less, while the capacitors in the energy storage capacitor network 26 may be charged to 1500 volts or more. A charge voltage control signal from the controller 18 determines the charge voltage on each capacitor in an energy storage capacitor network 26.

The energy storage capacitor network 26 according the present invention contains multiple capacitors which may be arranged in series, parallel, or a combination of series and parallel arrangements responsive to a configuration control signal from the controller 18. The energy storage capacitor network 26 has an effective capacitance and effective charge voltage that depend on the selected configuration. For example, a configuration that consists of three series capacitors with a capacitance value C and charge voltage V will have an effective capacitance of ⅓ C and effective voltage of 3 V.

The controller 18 uses the patient impedance and the selected energy level to select a configuration of the energy storage capacitor network 26 from the set of configurations in order to deliver the impedance-compensated defibrillation pulse to the patient. The operation of the energy storage capacitor network 26 in delivering the impedance-compensated defibrillation pulse is described in more detail below.

The energy storage capacitor network 26 is connected to the HV switch 16 which operates to deliver the defibrillation pulse across the pair of electrodes 12 to the patient in the desired polarity and duration response to the polarity/duration control signal from the controller 18. The HV switch 16 is constructed using an H bridge to deliver biphasic defibrillation pulses in the preferred embodiment but could readily be adapted to deliver monophasic or multiphasic defibrillation pulses and still realize the benefits of the present invention.

Figure 2:
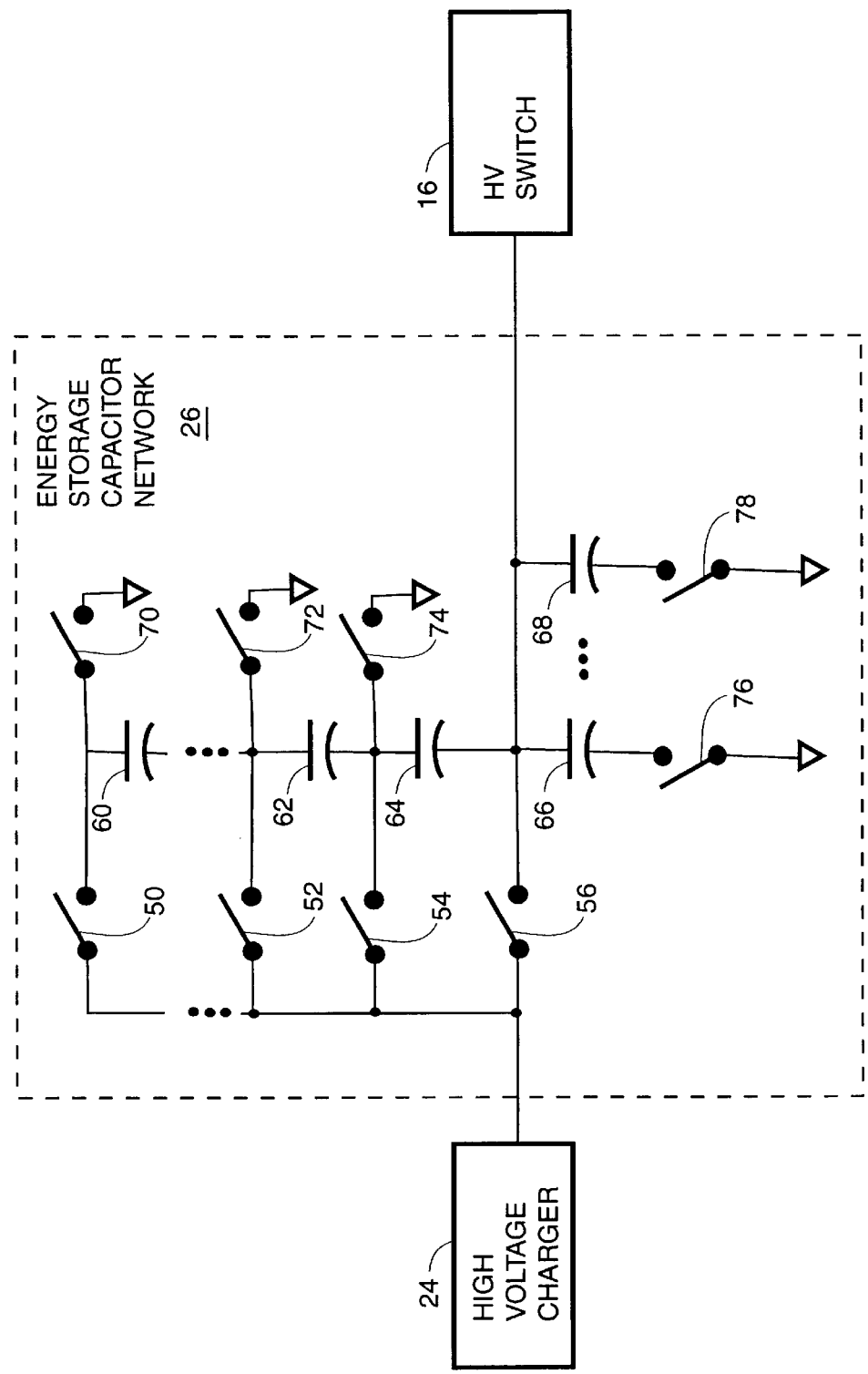
FIG. 2 is a schematic diagram of the energy storage capacitor network according to the present invention.

In FIG. 2, there is shown a simplified schematic of the energy storage capacitor network 26. The high voltage charger 24 is selectively connected to each of a set of capacitors 60–68 via a set of charging switches 50–56 to facilitate charging the capacitors 60–68 to a desired voltage level. Charging each of the capacitors 60–68 be either done sequentially or simultaneously in parallel as needed and with each of the capacitors 60–68 charged to either the same voltage level or different voltage levels according to the requirements of the application. The set of capacitors 60–68 may have the same capacitance value or have different capacitance values depending on the application. In the preferred embodiment, each of the capacitors 60–68 has the same capacitance value and is charged to the same initial voltage. The set of charging switches 50–56 are controlled by the controller 18 to facilitate the charging process. A set of blocking diodes may be substituted for the set of charging switches 50–56 to facilitate the charging of the capacitors 60–68. Each of the switches 50–56 and 70–78 is preferably controlled by the controller 18 via a set of control lines to each of the switches 50–56 and 70–78 (not shown).

A set of switches 70–78 coupled between the switches 60–68 and ground provide for creating the desired series, parallel, or series-parallel circuits. The capacitors 60–64 are shown coupled in series, with the series capacitors numbering as many as needed or as few as one. Similarly, the capacitors 66–68 are shown coupled in parallel. The number of parallel capacitors can be scaled up to as many as needed to obtain the desired effective capacitance necessary to deliver the desired energy level in the impedance-compensated defibrillation pulse.

Obtaining higher energy levels in the defibrillation pulse without increasing the charge voltage or encountering current levels that exceed the maximum level may be done by adding parallel capacitors to selected series or parallel capacitor combinations in a manner that increase the overall effective capacitance without increasing the charge voltage. For example, if a configuration for the series arrangement of the capacitors 62 and 64 is called for to obtain a desired voltage level for a given patient impedance but a higher level of capacitance is needed to obtain the desired energy level, additional capacitors (not shown) can be placed in parallel with each of the capacitors 62 and 64 using additional switches.

Obtaining energy levels above 200 joules (j) may be achieved in this manner using 100 uF capacitors without increasing the charge voltage level above 2,000 volts. Such higher energy level options could be available as additional configurations in the set of configurations of the energy storage capacitor network 26. The versatility of selecting among the configurations allows higher levels of energy to be delivered by the impedance-compensated defibrillation pulse while avoiding current levels that exceed the maximum value.

The capacitors 60–68 are coupled in one of a selected configuration from a set of series, parallel, or series-parallel configurations to the HV switch 16 under the control of the controller 18 which determines the polarity and duration of the impedance-compensated defibrillation pulse to the patient. In the preferred embodiment, the selected configuration of the energy storage capacitor network 26 remains constant throughout each phase of the defibrillation pulse, such as the first and second phases of a biphasic defibrillation pulse. Alternatively, the selected configuration may be changed between phases, such as to obtain additional energy transfer during the second phase.

Figure 3:
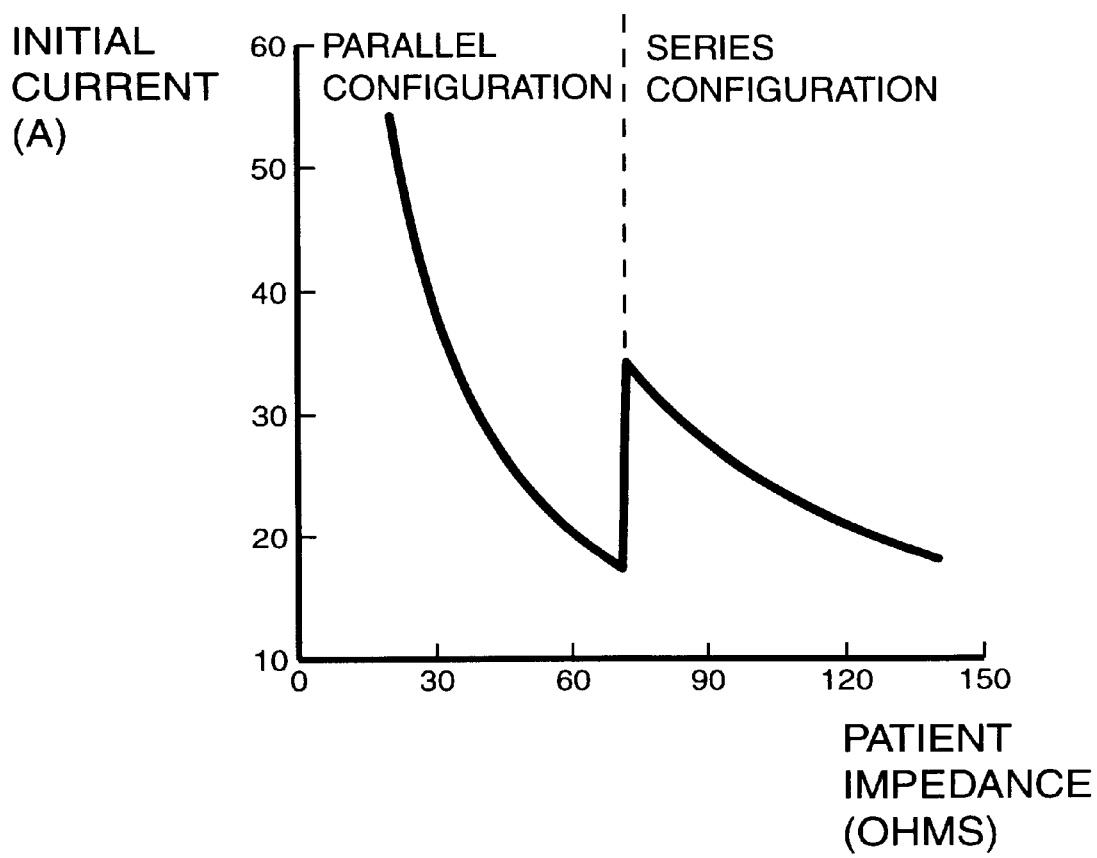
FIG. 3 is a graph of initial current versus patient impedance using the energy storage capacitor network according to the present invention.
Figure 4A:
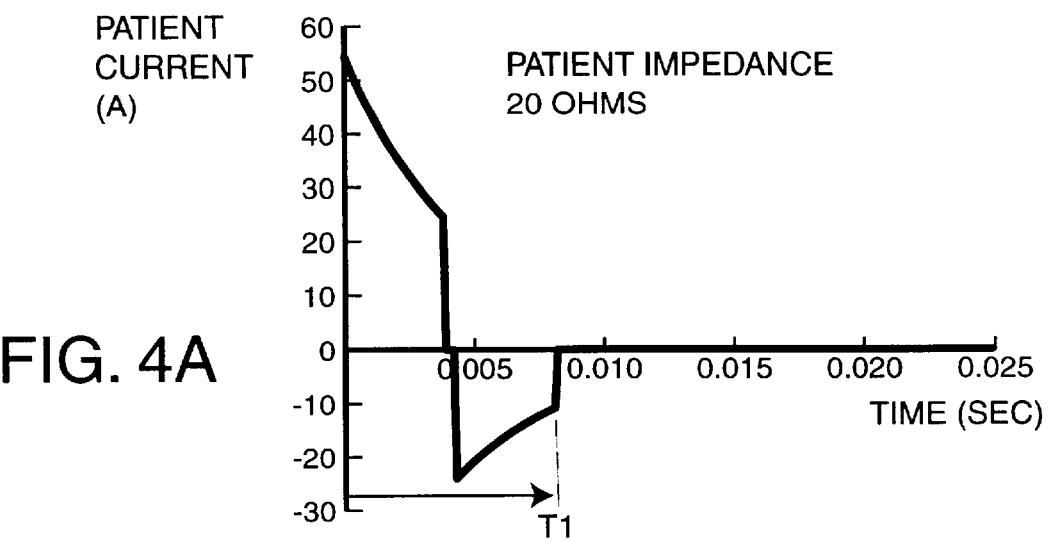
FIGS. 4A–C are a set of graphs of patient current over time for patient impedances of 20, 50, and 120 ohms respectively using the energy storage capacitor network according to the present invention.
Figure 4B:
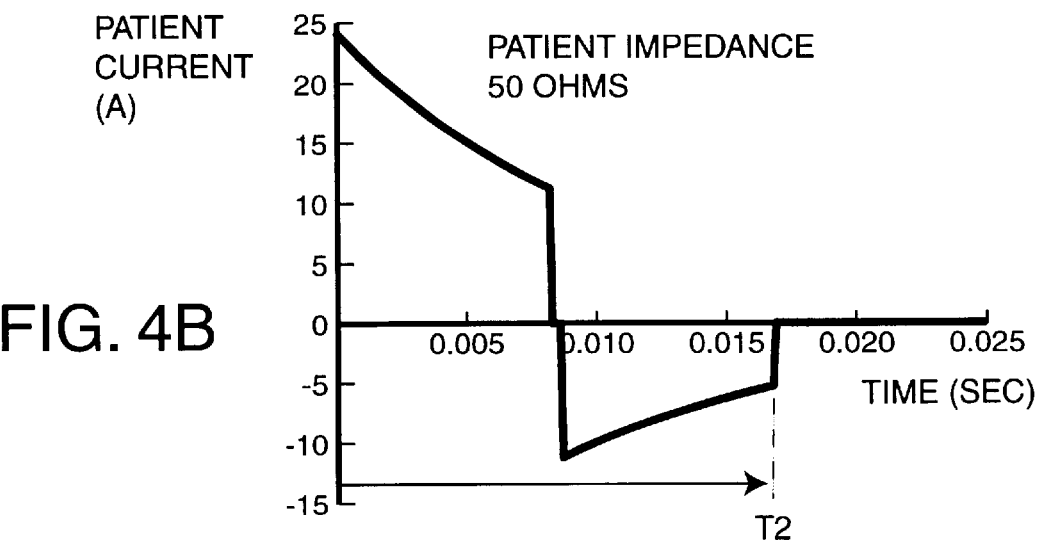
Figure 4C:
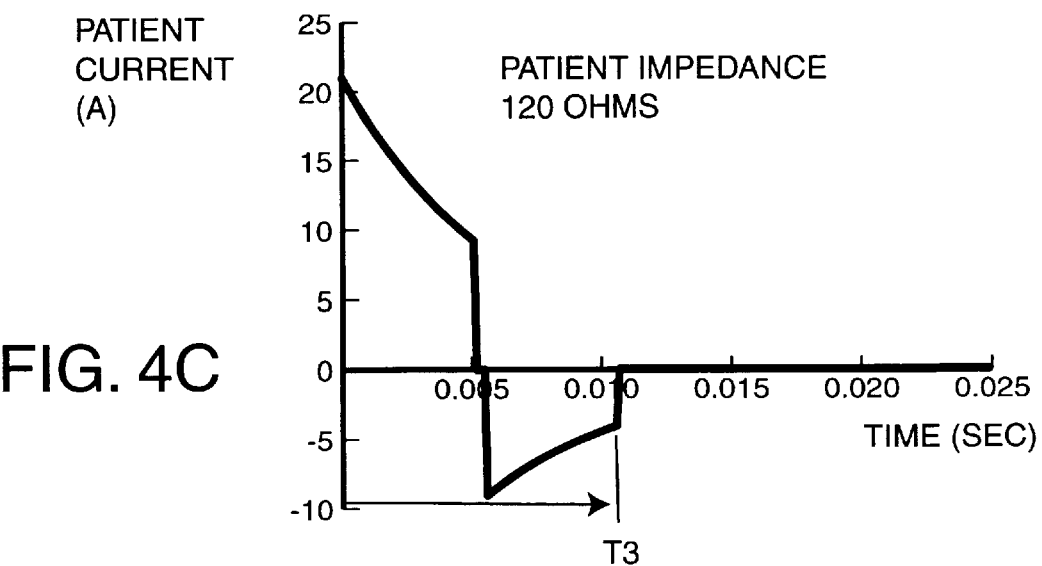
Figure 5:
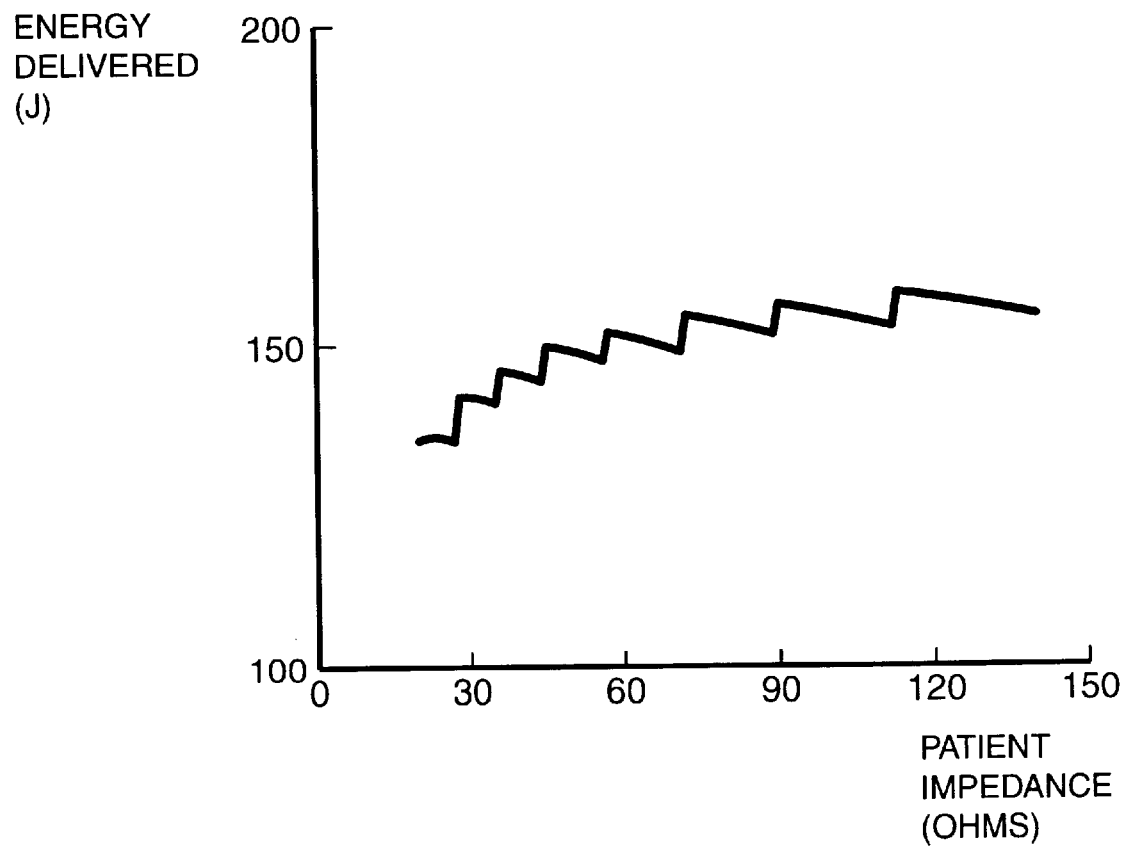
FIG. 5 is a graph of energy delivered versus patient impedances using the energy storage capacitor network according to the present invention.

In FIGS. 3, 4, and 5 that follow, the operation of the energy storage capacitor network 26 using a set of two configurations is illustrated for purposes of example. A series configuration employs two 100 microFarad (uF) capacitors coupled in series and is selected for patient impedances above 72 ohms. A parallel configuration employs two 100 uF capacitors coupled in parallel and is selected for patient impedances below 72 ohms. The value of 72 ohms was arbitrarily chosen as the delineation between high impedance and low impedance patients. The energy level remains fixed at 150 joules in this example, leaving just the two configurations of the energy storage capacitor network 26 in the set that are selected by the controller 18 based on impedance.

The same two 100 uF capacitors may be used for both the series and parallel configurations according to this example or different capacitors may be may be selected within the energy storage capacitor network 26. Additional series, parallel, and series-parallel configurations of capacitors may be readily added to allow for closer compensation of the defibrillation pulse for the patient impedance as explained above. The energy level can be increased by adding configurations that provide for parallel capacitors that are addd to the existing configuration to increase its equivalent capacitance without increasing the total voltage or peak current delivered to the patient in the defibrillation pulse.

FIG. 3 is a graph of initial current versus patient impedance. Initial current is equivalent to peak current since the peak current occurs at the initial application of the defibrillation pulse. As shown in the graph, a discontinuity appears at 72 ohms where the changeover is made by the controller 18 between the series and parallel configurations based on the patient impedance measured by the front end 14. In the region below 72 ohms, the parallel configuration is selected in the energy storage capacitor network 26 in which the 100 uF capacitors, each charged to 1300 volts, are coupled in parallel. This parallel configuration is equivalent to a single 200 uF capacitor charged to 1300 volts. In the region above 72 ohms, the series configuration is selected in the energy storage capacitor network 26 in which the 100 uF capacitors are coupled in series. This series configuration is equivalent to a single 50 uF capacitor charged to 2600 volts.

The use of the series and parallel configurations corresponding to the patient impedances below and above the cutoff resistance of 72 ohms respectively allows for peak currents to remain below a maximum value of 60 amperes for low impedance patients and above 15 amperes for high impedance patients. In this way, an impedance-compensated defibrillation pulse is delivered to the patient by the defibrillator 10.

FIGS. 4A–C are a set of graphs showing patient current versus time to form the defibrillation pulses for the patient impedances of 20 ohms, 50 ohms, and 120 ohms respectively. Each of the defibrillation pulses in this example is a biphasic truncated exponential (BTE) type pulse. The energy storage capacitor network 26 according to the present invention may be applied equally well for other types of defibrillation pulses including monophasic and multiphasic pulses. In this example, tilt, which is the percentage decrease in capacitor voltage, and pulse duration are controlled to regulate the amount of energy delivered to the patient by the defibrillation pulse. The peak current for each defibrillation pulse is the initial current at time 0 when the defibrillation pulse is first applied.

In comparing FIGS. 4A–C, the times t1, t2, and t3 are the duration times of the defibrillation pulses for the defibrillation pulse delivered to patients having impedances of 20 ohms, 50 ohms, and 120 ohms respectively. Time t2 for the 50 ohm impedance is greater than time t1 for the 20 ohm impedance since the parallel configuration is selected for patient impedances below 72 ohms and a longer duration is needed to deliver the required amount of energy. In FIG. 4C, the series configuration is selected for the 120 ohm impedance which requires a shorter duration of time t3 relative to time t2 to deliver the required amount of energy to the patient. In this way, the impedance-compensated defibrillation pulse is delivered over the 20 to 200 range of patient impedances with a smaller range of pulse duration times using the energy storage capacitor network 26 according to the present invention than by using a single energy storage capacitor.

More configurations of the energy storage capacitor network 26 may be readily added to deliver an impedance-compensated defibrillation pulse that is more finely tailored to the patient impedance and increase the range of energy levels that may be delivered to the patient. The spread of duration times of the defibrillation pulses across the range of patient impedances would narrow as further configurations are added to the set of possible configurations of the energy storage capacitor network 26.

FIG. 5 is a graph of energy delivered over the range of patient impedances. It is desirable that the delivered energy delivered not be reduced for high patient impedances. In the preferred embodiment, the plot shown is acceptably flat for the chosen application with energy delivered in the range of 130 to 160 joules.

As shown in the graph, the plot of energy delivered versus patient impedance consists of piecewise segments. The piecewise segments are artifacts of the control algorithm in the preferred embodiment in which the capacitors elements and duration times are selected from a finite set of values. The number of piecewise segments thus depends on the capacitor elements and granularity of the set of duration times. Alternatively, the plot shown in FIG. 5 could be drawn as a smooth curve rather than as piecewise segments if a control system that allowed for continuous variation in duration times were to be employed.

The use of an impedance-compensated defibrillation pulse according to the present invention allows for a selected energy level, such as 150 joules, to be delivered with an acceptable level of accuracy, to a patient of unknown impedance within the range of 20 to 200 ohms, and with both pulse duration and peak current within predetermined limits. Impedance-compensated defibrillation pulses having higher energy levels in excess of 200 joules can be achieved with the addition of configurations to the set of configurations of the energy storage capacitance network 26 providing for added parallel capacitors.

Figure 6:
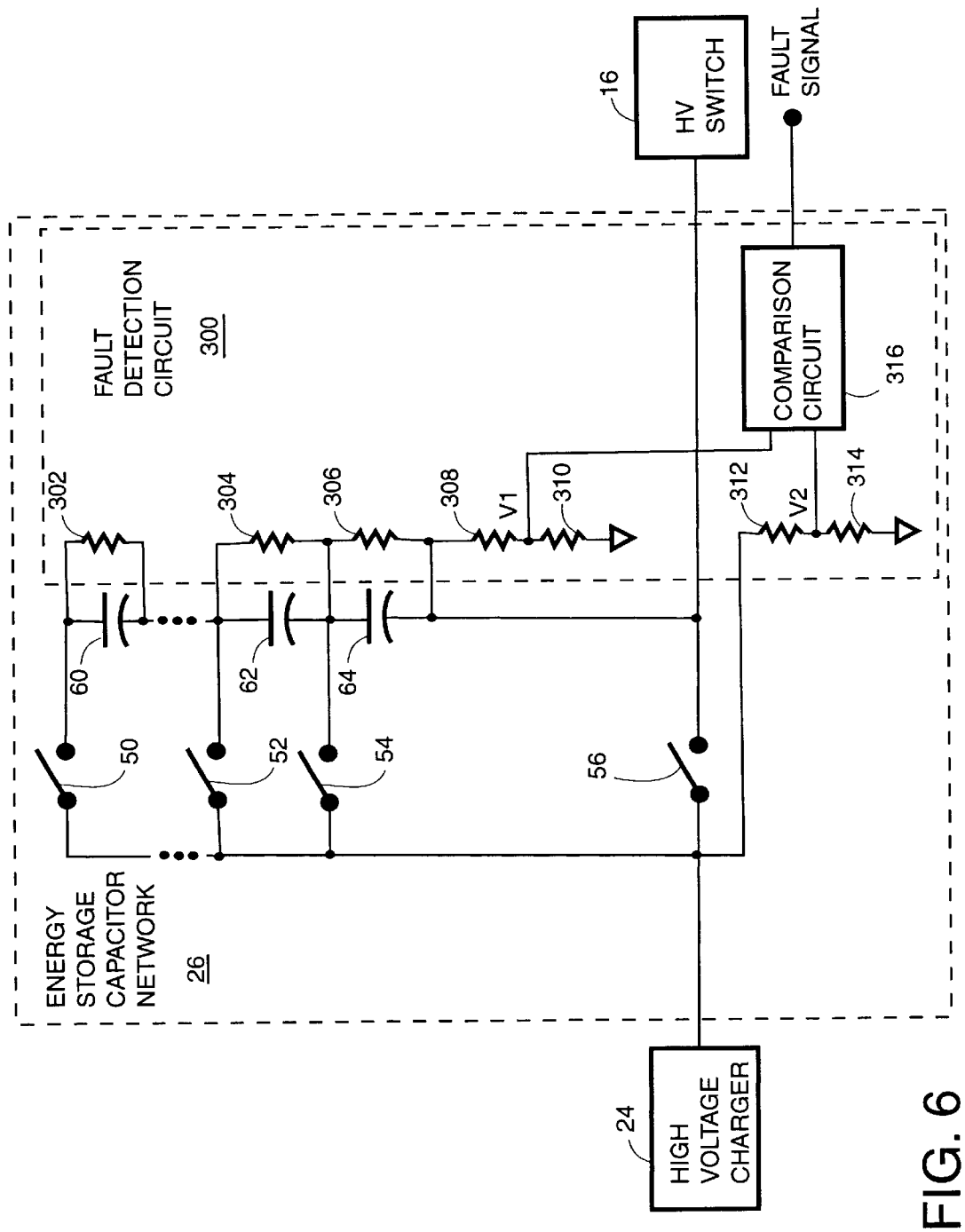
FIG. 6 is a schematic diagram of a fault detection circuit as applied in the energy storage capacitor network.

FIG. 6 is a schematic drawing of a fault detection circuit 300 that may be employed in the energy storage capacitor network 26 to detect faults. Because the capacitors 60–64 are charged to relatively high voltages in the range of 1500 volts and the voltages in a series connection of charged capacitors is additive, directly detecting faults in any one capacitor is difficult. Variations in the voltages generated by the high voltage charger 24 must also be controlled for in order to isolate faults which appear as voltage differences between the capacitors. The fault detection circuit 300 operates to detect faults in series capacitors which may be charged to high voltages by generating a relatively low first and second test voltages that can be compared using relatively simple comparators to detect faults.

The fault detection circuit 300 consists of a series network of resistors 302–310, with the resistors 304–306 coupled across the capacitors 60–64 respectively and resistors 308–310 are further coupled in series between the resistors 302–306 and ground to form a tap for developing a first test voltage V1. The first test voltage V1 may be subsequently compared with a second test voltage V2 developed at the voltage divider formed by resistors 312 and 314 which connected across the high voltage charger 16. The resistor values for the resistors 302–314 are chosen to be relatively high, typically above 1 MegOhm, in order to avoid interference with the normal operation of the energy storage capacitor network 26.

The values of the resistors 302–314 can be chosen so that V1=V2 within a predetermined limit for normal operation and so that V1 differs from V2 by greater than the predetermined limit to detect a fault condition such as a leaky capacitor. The use of the test voltage V2 allows for variations in the voltage generated by the high voltage charger 24 to be controlled for. The first and second test voltages V1 and V2 are provided to a comparison circuit 316 which generates a fault signal in response to the condition in which V1 differs from V2 by greater than the predetermined limit. The comparison circuit 316 may be implemented using a low cost comparators and standard digital logic. Alternatively, V1 and V2 may be measured to obtain digital data that can then be compared using a microprocessor to detect the fault condition.

A fault condition in the energy storage capacitor network 26 occurs when at least one of the capacitors 60–64 exhibits excessive leakage current such that it begins to self discharge, resulting in changes in its charge voltage. The fault condition can be readily detected using the fault detection circuit 300 because the voltage differential in the faulty capacitor would result in a change in the first test voltage V1. The fault detection circuit 300 may be readily scaled to the number of series capacitors in the fault detection circuit 300.

Figure 7:
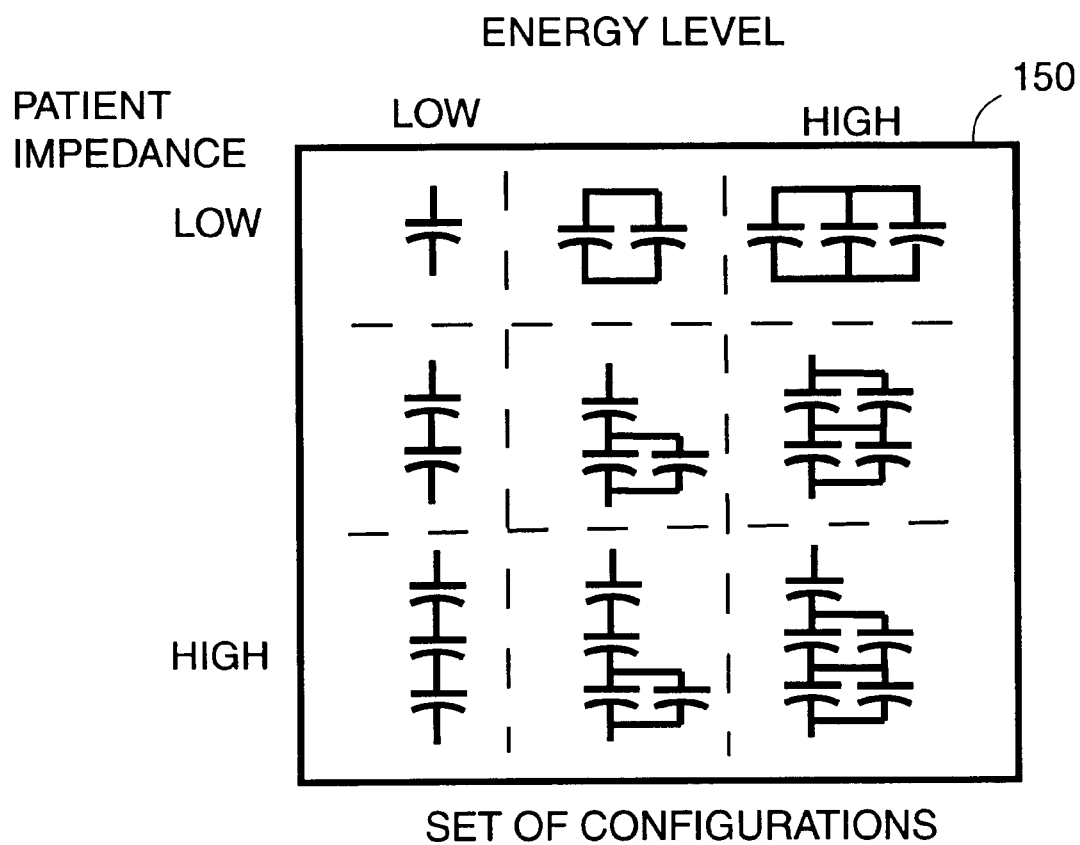
FIG. 7 is an illustration of a set of configurations of the energy storage capacitor network which may be selected according to the patient impedance and desired energy level according to the present invention.

In FIG. 7 there is shown an illustration of a set of configurations 150 of the energy storage capacitor network 26 which may be selected according to the patient impedance and desired energy level according to the present invention. The set of configurations 150 is shown for purposes of example as a matrix to illustrate the process of selecting a configuration based on the patient impedance and the desired energy level. Along the vertical axis is the range of patient impedances ranging from low to high. Along the horizontal axis is the desired energy level, ranging from low to high.

The energy level delivered to the patient in the defibrillation pulse is largely determined by the capacitance, voltage, and waveform duration. By selecting a configuration from the set of configurations 150 according to the desired energy level prior to delivery of the defibrillation pulse, a wider range of energy levels can be generated without causing patient currents that exceed the maximum value and without a defibrillation pulse having excessively long discharge times.

As shown in the set of configurations 150, higher impedance patients generally require higher voltages in the defibrillation waveform and connecting capacitors in series to obtain the higher voltage may be done. Conversely, lower impedance patients generally require lower voltages to avoid peak currents in excess of the maximum value. Obtaining higher higher energy delivery such as in the region above 200 j to the patient may be accomplished by adding parallel capacitors to the existing configuration selected as a function of patient impedance.

Many variations on the set of configurations 150 may be constructed to tailor the operation of the energy storage capacitor network 26 to the particular requirements of the defibrillator 10. For example, in an AED in which the desired energy level is fixed at one energy level such as 150 joules, only a single column of the matrix shown in the set of configurations 150 need be employed. The controller 18 would then select from the set of configurations based only on the patient impedance prior to delivering the impedance-compensated defibrillation pulse.

Figure 8:
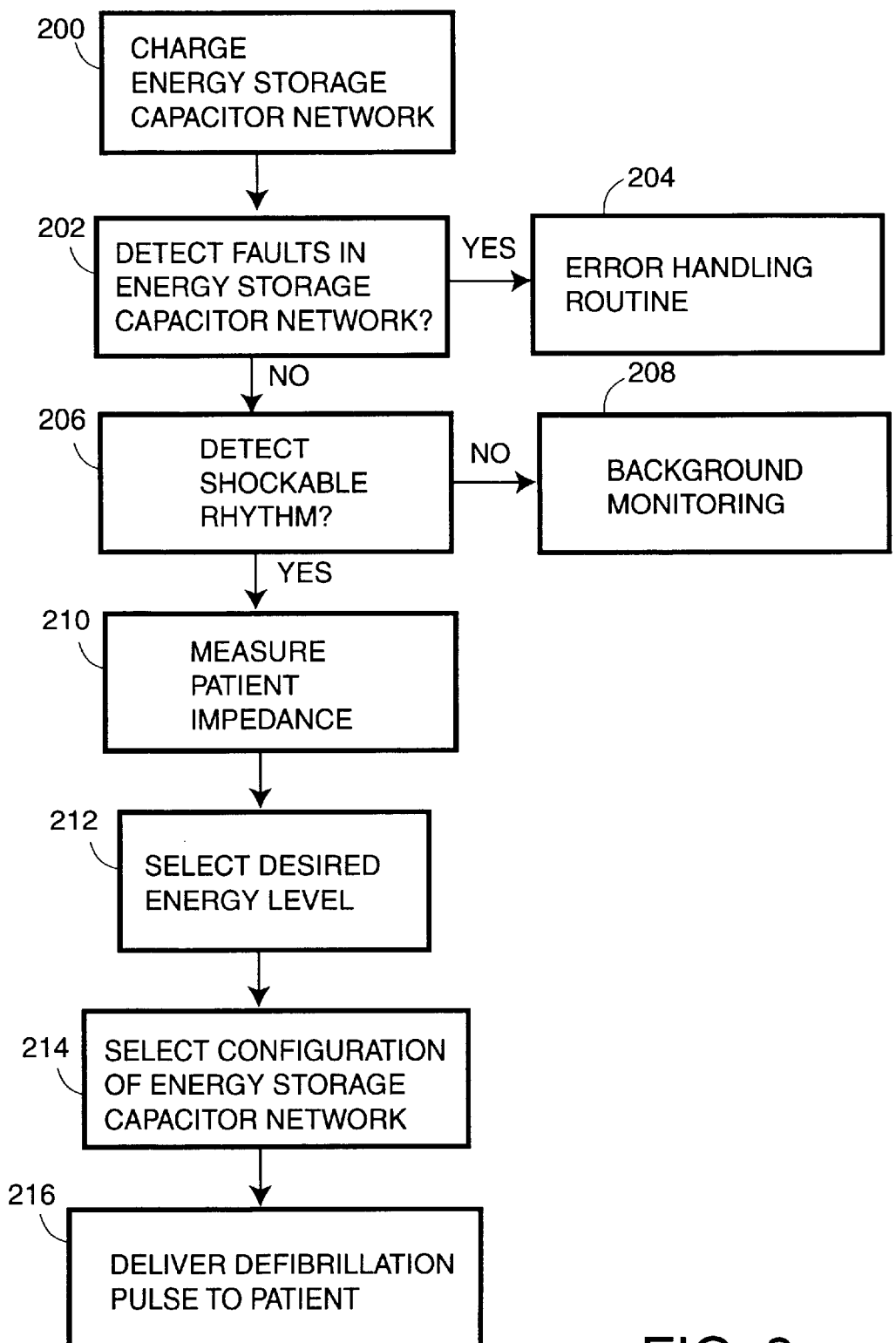
FIG. 8 is a flow diagram of the process of delivering an impedance-compensated defibrillation pulse based on the method according to the present invention.

In FIG. 8 there is shown a flow diagram of the process of delivering an impedance-compensated defibrillation pulse by the defibrillator 10 based on the method according to the present invention. In step 200 labeled CHARGE ENERGY STORAGE CAPACITOR NETWORK, the high voltage charger 24 operates to charge each of the capacitors of the energy storage capacitor network 26 in preparation for delivery of a defibrillation pulse. Such charging can be done immediately upon activation of the defibrillation 10 in which the capacitors are charged to a predetermined percentage of the desired voltage level in order to conserve energy and save charging time in case the defibrillation pulse will be needed.

In step 202 labeled DETECT FAULTS IN ENERGY STORAGE CAPACITOR NETWORK, the fault detection circuit 300 may be employed to detect faults within the energy storage capacitor network 26 such as a leaky capacitor that fails to hold its charge voltage within a predetermined limit. If a fault is detected, step 204 labeled ERROR HANDLING ROUTINE will generate an error message alerting the operator to the failure condition. Other diagnostic circuits could be activated to isolate the fault and possibly allow the defibrillator 10 to operate in a limited functionality by inactivating the portions of the set of configurations 150 that employ the damaged area.

In step 206 labeled DETECT SHOCKABLE RHYTHM?, the controller 18 executes a shock advisory algorithm to detect a shockable rhythm such as ventricular fibrillation (VF). If no shockable rhythm is detected, step 208 labeled BACKGROUND MONITORING is executed in which the operator is informed that no shock is advised and the defibrillator 10 goes into a background monitoring mode in which the ECG information continues to be monitored and analyzed.

If a shockable rhythm is detected, step 210 labeled MEASURE PATIENT IMPEDANCE is executed. The patient impedance is measured and supplied to the controller 18 through any of a variety of methods such as delivery of a non-therapeutic pre-shock or measurement of low level test signals.

In step 212 labeled SELECT DESIRED ENERGY LEVEL, the energy level of the defibrillation pulse to be delivered to the patient is determined. In many cases, the energy level is predetermined to be a fixed level such as 150 joules such as in an AED. In other cases, a defibrillation protocol determines the energy level based on the number of defibrillation pulses that are delivered. For example, the commonly used protocol for three successive monophasic defibrillation pulses calls for calls for energy levels of 200 joules followed by 300 joules and 360 joules. The energy level may also be manually determined such as in a manual defibrillator, allowing the operator to determine the desired energy level via a user interface setting.

In step 214 labeled SELECT CONFIGURATION OF ENERGY STORAGE CAPACITOR NETWORK, the patient impedance and the desired energy level are now used as parameters by the controller 18 in the selection of the appropriate configuration from the set of configurations 150 in the energy storage capacitor network 26. Once a selection is made, the controller 18 sends the configuration signal to the energy storage capacitor network 26 to actuate the switches and implement the desired configuration.

The desired energy level may be selected on the basis of patient impedance. For example, it may be desirable to deliver a higher desired energy level to a high patient impedance and a lower desired energy level to a low patient impedance. The patient impedance and desired energy level, though no longer independent variables, would still be used as parameters by the controller 18 as described above to select of the appropriate configuration from the set of configurations 150. Coupling the parameters in this way, with the desired energy level as a dependent variable upon the patient impedance, may allow for more efficacious defibrillation where it is found that different patient impedances respond better to defibrillation pulses having different energy levels.

In step 216 labeled DELIVER DEFIBRILLATION PULSE TO PATIENT, the defibrillator 10 signals the operator to press the shock button 20 to initiate delivery of the defibrillation pulse to the patient. The controller 18 determines the polarity and duration of the defibrillation pulse according to such parameters as waveform tilt in order to provide the desired amount of energy and waveshape such as biphasic truncated exponential.

Figure 9:
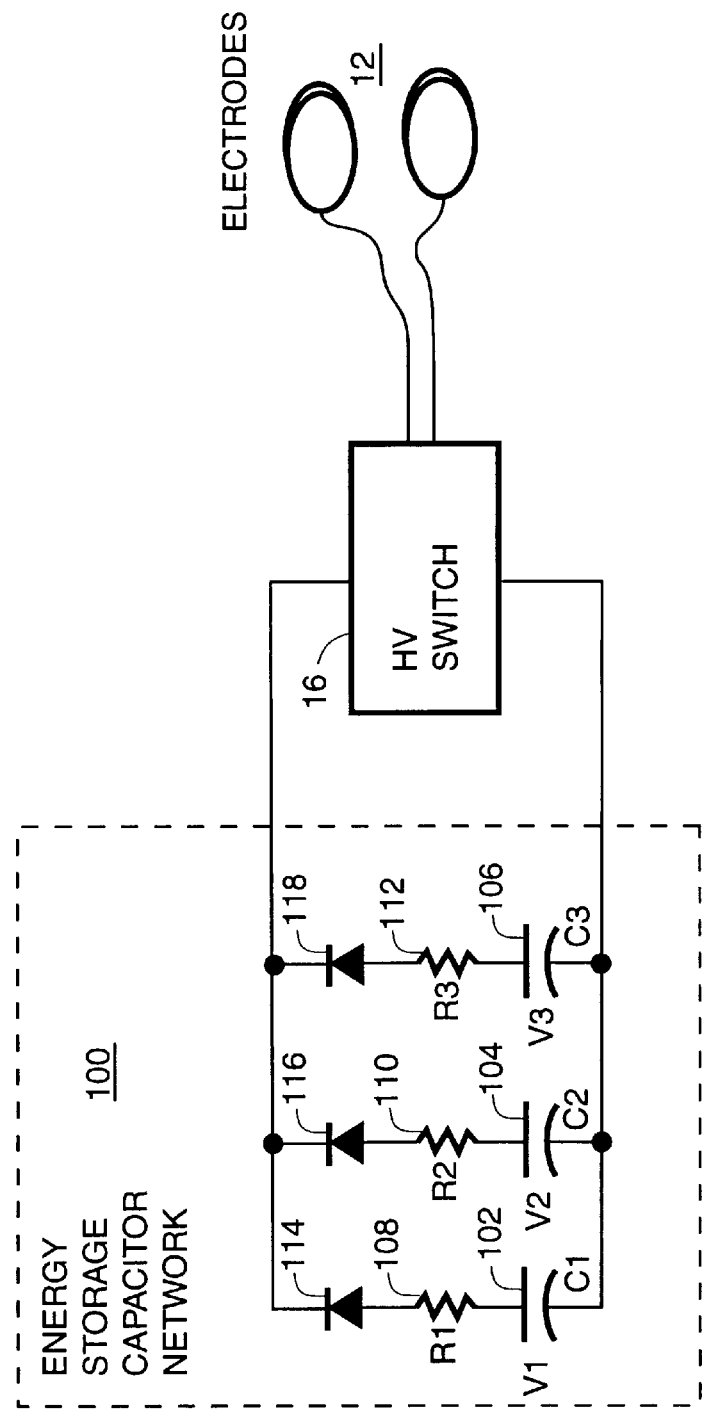
FIG. 9 is schematic diagram of the energy storage capacitor network according to an alternative embodiment of the present invention.

FIG. 9 is a schematic diagram of an energy storage capacitor network 100 according to an alternative embodiment of the present invention which may be substituted for the energy storage capacitor network 26 described above. Capacitors 102, 104 and 106 are placed in series with resistors 108, 110, and 112 and diodes 114, 116, and 118. Each of the series combinations of capacitors 102–106, resistors 108–112, and diodes 114–118 form sections that supply energy to the HV switch 16 to generate the defibrillation pulse. Each of the sections is connected in parallel to deliver energy to through the HV switch 16 and the pair of electrodes 12 to the patient. The HV switch 16 may be controlled to deliver the defibrillation pulse in the desired polarity and duration to create monophasic, biphasic, or multiphasic waveforms as desired. Additional sections may be added as needed to the energy storage capacitor network 100 or as few as two sections may be used according to the alternative embodiment.

For purposes of example, the three sections in the energy storage capacitor network 100 are illustrated. The capacitors 102–106 have capacitance values $C_1$, $C_2$, and $C_3$ respectively and charge voltage levels $V_1$, $V_2$, and $V_3$ respectively which are chosen in conjunction with the values $R_1$, $R_2$, and $R_3$ for the resistors 108–112 to deliver the impedance-matched defibrillation pulse over the desired range of patient impedances at a desired energy level. In this example, the values were chosen according to the following rank order relationships:

$C_1 \geq C_2 \geq C_3$ $V_1 > V_2 > V_3$ $R_1 > R_2 > R_3$

According to these relationships, the capacitance values $C_1$, $C_2$, and $C_3$ can be the same value or assume the sized ordered relationship shown according to the application requirements. The voltage values $V_1$, $V_2$, and $V_3$ and resistance values $R_1$, $R_2$, and $R_3$ are in rank order in order to ensure the sequential discharge of the three sections. Sequential discharge means that as one section discharges below a predetermined level, another section will begin to discharge. The timing of the discharge sequence is driven by the discharge times of the sections and the component values are chosen to obtain desired discharge times over the range of patient impedances. The magnitude of the values for $R_1$–$R_3$, $C_1$–$C_3$, and $V_1$–$V_3$ are also chosen to deliver the desired energy level in the defibrillation pulse to the patient.

Figure 10A:
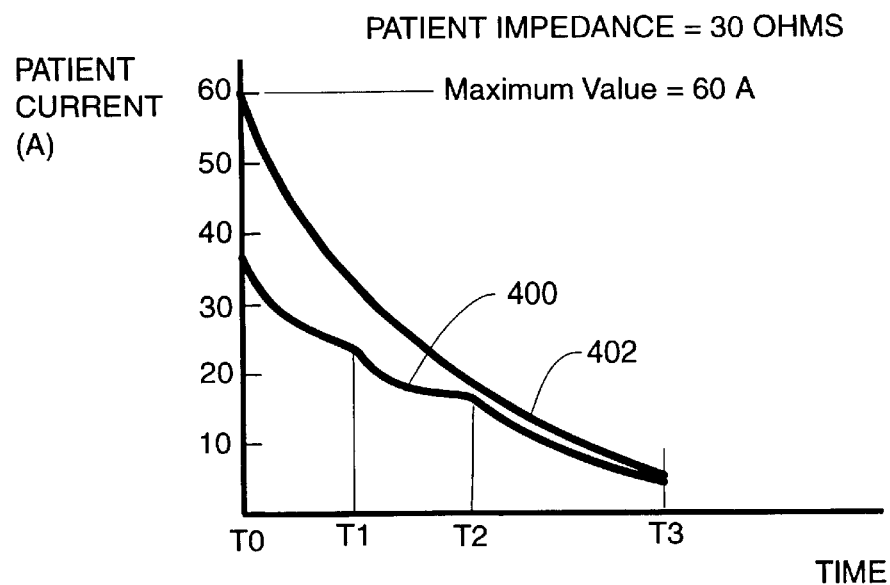
FIGS. 10A and 10B are graphs of patient current over time for low impedance and high impedance patients using the energy storage capacitor network according to the alternative embodiment of the present invention shown in FIG. 9.
Figure 10B:
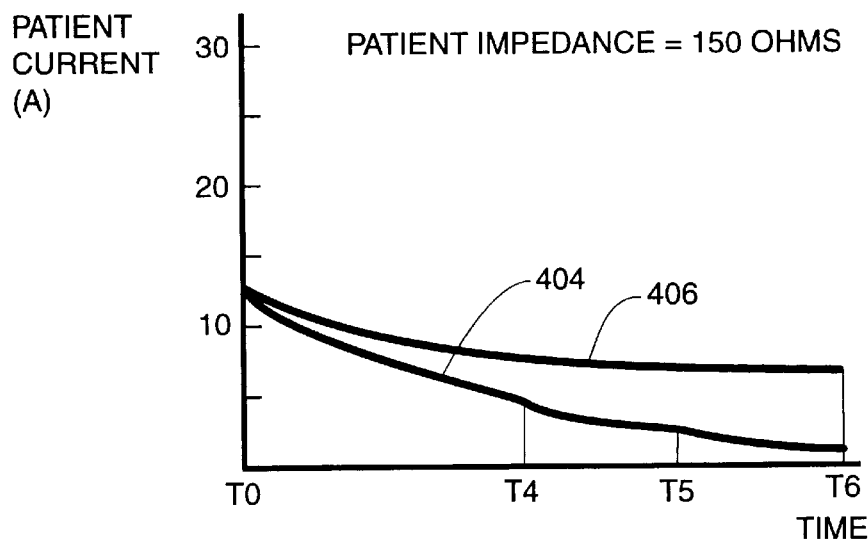

FIGS. 10A and 10B are graphs of patient current over time for low impedance and high impedance patients using the energy storage capacitor network 100 according to the alternative embodiment of the present invention shown in FIG. 9. FIG. 10A is a graph of defibrillation pulses for a patient impedance of 30 ohms which is at the lower end of the range of patient impedances. Trace 400 illustrates a patient current versus time waveform of a defibrillation pulse which is possible using the energy storage capacitor network 100. Trace 402 is a defibrillation pulse of a typical patient current obtained using a single capacitor according to the prior art. While the defibrillation pulses are shown as monophasic types, biphasic and multiphasic defibrillation pulses can also be generated using the HV switch 16.

Trace 400 is shown with segments spanning times T0–T1, T1–T2, and T2–T3. The segment spanning T0–T1 is the discharge current from the first section consisting of capacitor 102, resistor 108, and diode 114. The capacitor 102 with capacitance $C_1$ is charged to the highest voltage level $V_1$ with the largest value of resistance $R_1$. The diode 114 is forward biased and the first section discharges first before the other two sections. As the first section discharges below the charge level $V_2$ of the second section consisting of the capacitor 102, resistor 108, and diode 114 at time T1, the diode 114 becomes forward biased to begin the discharge of the second section. As the second section discharges below the charge voltage $V_3$ of the third section consisting of the capacitor 104, resistor 110, and diode 116 at time T2, the diode 116 becomes forward biased to begin the discharge of the third section which continues to time T3. Time T3 occurs when when the HV switch is opened responsive to the polarity/duration signal from the controller 18.

The trace 400 has a peak current of 36 A at time T0. By contrast, the trace 402 has a peak current of 60 A according to a single capacitor charged to 1800 V. To generate the defibrillation pulse according to trace 400, the first section of the energy storage capacitor network 100 is constructed using the capacitor 102 charged to 2160 V which is in series with the resistor 108 having a value $R_1$ of 30 ohms which operates to limit the peak current to 36 A. The second and third sections, employing lower resistance values $R_2$ and $R_3$ as well as lower charge voltages $V_2$ and $V_3$ operate to deliver the desired amount of energy in the remaining portion of the defibrillation pulse.

FIG. 10B is a graph of defibrillation pulses for a patient impedance of 150 ohms which is at the upper end of the range of patient impedances. Trace 404 illustrates a patient current versus time waveform of a defibrillation pulse which is possible using the energy storage capacitor network 100. Trace 406 is a defibrillation pulse of a typical patient current obtained using a single capacitor according to the prior art.

Trace 404 is shown with segments spanning times T0–T4, T4–T5, and T5–T6. The energy storage capacitor network 100 operates in the same manner as described above for the low patient impedance example for the three segments. Traces 404 and 406 both have peak currents of 12 A. Over the time period spanning T0 to T6, trace 404 exhibits a faster current decay than trace 406. In this way, the range of durations of the defibrillation pulse may be kept smaller over the range of patient impedances.

FIGS. 10A and 10B illustrate the method of delivering an impedance-compensated defibrillation pulse which has peak currents less than the maximum value for low patient impedances and with limited pulse durations for high patient impedances as described above. Additional sections could be added as needed. The high voltage charger 24 would be configured to charge each of the capacitors 102–106 to the charge voltages $V_1$–$V_3$ respectively in order to charge the energy storage capacitor network 100 in preparation for delivery of the impedance compensated defibrillation pulse.

It will be obvious to those having ordinary skill in the art that many changes may be made in the details of the above-described preferred embodiments of the invention without departing from the spirit of the invention in its broader aspects. For example, a variety of switch technologies, ranging from mechanical switches to various types of solid state switches may be employed in the energy storage capacitor network 26. The set of possible configurations of the energy storage capacitor network may be readily expanded or reduced to suit the application requirements including closeness of impedance-compensation and desired range of available energy levels. Therefore, the scope of the present invention should be determined by the following claims.

What we claim as our invention is:

1. A defibrillator comprising:
   a pair of electrodes for coupling to a patient;
   an HV switch coupled to said pair of electrodes; and
   a configurable energy storage capacitor network for delivering an impedance-compensated defibrillation pulse through said HV switch to said patient
   a controller for obtaining a patient impedance and coupled to said energy storage capacitor network to select one of a plurality of configurations based on said patient impedance.

2. A defibrillator according to claim 1 wherein said energy storage capacitor network comprises a plurality of capacitors that are arranged according to a plurality of configurations.

3. A defibrillator according to claim 2 further comprising a high voltage charger coupled to said energy storage capacitor network for charging each of said capacitors.

4. A defibrillator according to claim 3 further comprising a set of charging switches interposed between said high voltage charger and each of said capacitors.

5. A defibrillator according to claim 2 further comprising:
   a front end coupled to said pair of electrodes to provide a patient impedance; and
   wherein said controller is coupled to said front end to obtain said patient impedance and to said energy storage capacitor network to select one of said plurality of configurations based on said patient impedance and a selected energy level.

6. A defibrillator according to claim 5 wherein said controller is coupled to said HV switch to control a duration and polarity of said impedance-compensated defibrillation pulse.

7. A defibrillator according to claim 6 wherein said impedance-compensated defibrillation pulse comprises one of monophasic, biphasic, and multiphasic.

8. A defibrillator according to claim 5 wherein said controller selects one of said configurations based on a fixed selected energy level.

9. A defibrillator according to claim 5 wherein said controller determines said selected energy level according to a protocol.

10. A defibrillator according to claim 5 wherein said controller selects one of said configurations based on an energy level manually selected by a user.

11. A defibrillator according to claim 5 wherein said selected energy level is determined as a function of said patient impedance.

12. A defibrillator according to claim 2 wherein said energy storage capacitor network further comprises:
    a plurality of capacitors coupled in series and in parallel to said HV switch; and
    a plurality of switches coupled between each of said capacitors and ground,
    wherein said energy storage capacitor network is configured to deliver an impedance-compensated defibrillation pulse by setting said plurality of switches according to one of said configurations.

13. A defibrillator according to claim 1 wherein said impedance-compensated defibrillation pulse has a peak current less than a maximum value.

14. A defibrillator according to claim 1 wherein said energy storage capacitor network comprises:
    a plurality of sections, each of said sections comprising a capacitor, a resistor, and a diode coupled in series and each of said sections coupled in parallel to said HV switch;
    wherein each of said capacitors is charged to a charge voltage according to a rank order and each of said resistors is has a resistance chosen according to said rank order wherein said energy storage capacitor network is configured to deliver an impedance-compensated defibrillation pulse by sequentially discharging each of said sections.

15. A method for delivering an impedance-compensated defibrillation pulse to a patient, comprising:
    measuring a patient impedance of said patient;
    selecting from a set of configurations in an energy storage capacitor network to deliver an impedance-compensated defibrillation pulse to said patient responsive to said patient impedance; and
    delivering said impedance-compensated defibrillation pulse to said patient.

16. A method for delivering an impedance-compensated defibrillation pulse to a patient according to claim 15 further comprising selecting from said set of configurations responsive to a selected energy level.

17. A method for delivering an impedance-compensated defibrillation pulse to a patient according to claim 16 wherein said selected energy level is fixed at one level.

18. A method for delivering an impedance-compensated defibrillation pulse to a patient according to claim 16 wherein said selected energy level is determined according to a protocol.

19. A method for delivering an impedance-compensated defibrillation pulse to a patient according to claim 16 wherein said selected energy level is manually selected by a user.

20. A method for delivering an impedance-compensated defibrillation pulse to a patient according to claim 15 further comprising charging said energy storage capacitor network using a high voltage charger.

21. A method for delivering an impedance-compensated defibrillation pulse to a patient according to claim 15 further comprising coupling said patient to said energy storage capacitor network via a pair of electrodes.

22. A method for delivering an impedance-compensated defibrillation pulse to a patient according to claim 15 further comprising delivering said impedance-compensated defibrillation pulse to said patient with a peak current less than a maximum value.

23. A defibrillator comprising
    a pair of electrodes for coupling to a patient;
    a front end circuit coupled to said pair of electrodes to provide a patient impedance and an ECG signal;
    an HV switch coupled to said pair of electrodes;
    an energy storage capacitor network having a plurality of configurations; and
    a controller coupled to said front end, to said HV switch, and to said energy storage capacitor network;
    wherein said controller selects one of said configurations based on said patient impedance and a selected energy level and delivers an impedance-compensated defibrillation pulse through said HV switch to said patient responsive to detecting a shockable rhythm in said ECG signal.

24. A defibrillator according to claim 23 wherein said controller selects one of said configurations based on a fixed selected energy level.

25. A defibrillator according to claim 23 wherein said controller determines said selected energy level according to a protocol.

26. A defibrillator according to claim 23 wherein said controller selects one of said configurations based on an energy level manually selected by a user.

27. A defibrillator according to claim 23 wherein said selected energy level is determined as a function of said patient impedance.

28. A defibrillator according to claim 23 further comprising a high voltage charger coupled to said energy storage capacitor network for charging said energy storage capacitor network.

29. A defibrillator according to claim 23 wherein said controller determines a duration and a polarity of said impedance-compensated defibrillation pulse.

30. A defibrillator according to claim 23 wherein said impedance-compensated defibrillation pulse comprises one of monophasic, biphasic, and multiphasic.

31. A defibrillator according to claim 23 wherein said energy storage capacitor network provides for said selected energy level above 200 joules.

32. A defibrillator according to claim 23 wherein said energy storage capacitor network comprises:

a plurality of capacitors coupled in series and parallel to said HV switch; and a plurality of switches coupled between each of said capacitors and ground wherein said energy storage capacitor network is configured to deliver an impedance-compensated defibrillation pulse by setting said plurality of switches according to said one of said configurations.

33. A defibrillator according to claim 23 wherein said impedance-compensated defibrillation pulse has a peak current less than a maximum value.

34. A method for delivering an impedance-compensated defibrillation pulse to a patient, comprising:

providing a pair of electrodes for coupling to said patient;

providing an HV switch coupled to said electrodes;

providing a plurality of sections coupled in parallel in an energy storage capacitor network coupled to said HV switch, each of said sections comprising a capacitor, a resistor, and a diode coupled in series;

charging each capacitor to a charge voltage in said rank order with said other sections; and delivering an impedance matched defibrillation pulse through said HV switch and said pair of electrodes to said patient by sequentially discharging each of said sections.

35. A method for delivering an impedance-compensated defibrillation pulse to a patient according to claim 34 further comprising providing a controller coupled to said HV switch.

36. A method for delivering an impedance-compensated defibrillation pulse to a patient according to claim 35 wherein said controller determines a duration and a polarity of said impedance-compensated defibrillation pulse.

37. A defibrillator according to claim 36 wherein said impedance-compensated defibrillation pulse comprises one of monophasic, biphasic, and multiphasic.

38. In an energy storage capacitor network having a plurality of capacitors coupled in series and charged using a high voltage charger, a fault detection resistor network comprising:

a first resistor network coupled in shunt across each of said plurality of capacitors to develop a first test voltage;

a second resistor network coupled across said high voltage charger to develop a second test voltage; and a comparison circuit coupled to said first and second test voltages to generate a fault signal if said first test voltage differs from said second test voltage by greater than a predetennined limit.

* * * * *

Adverse Decision in Interference

Patent No. 6,241,751, Carlton B. Morgan, Bradford E. Gliner, Kent W. Leyde, Thomas D. Lyster, DEFIBRILLATOR WITH IMPEDANCE-COMPENSATED ENERGY DELIVERY, Interference No. 105,451, final judgment adverse to the patentees rendered February 20, 2008, as to claims 1-37.

*(Official Gazette July 29, 2008)*